(12) United States Patent
Tangellapally et al.

(10) Patent No.: US 7,426,475 B1
(45) Date of Patent: Sep. 16, 2008

(54) SECURE ELECTRONIC HEALTHCARE INFORMATION MANAGEMENT PROCESS AND SYSTEM

(76) Inventors: Mahesh Tangellapally, 5597 Le Fevre Dr., San Jose, CA (US) 95118; Ganesh Tangellapally, 3740 Armour Ct., Fremont, CA (US) 94555

( * ) Notice: Subject to any disclaimer, the term of this patent is extended or adjusted under 35 U.S.C. 154(b) by 1510 days.

(21) Appl. No.: 09/812,291

(22) Filed: Mar. 20, 2001

Related U.S. Application Data

(60) Provisional application No. 60/191,023, filed on Mar. 21, 2000.

(51) Int. Cl.
*A61B 5/00* (2006.01)
(52) U.S. Cl. ............................................. 705/3; 705/2
(58) Field of Classification Search .................... 705/2, 705/3
See application file for complete search history.

(56) References Cited

U.S. PATENT DOCUMENTS

| | | | | |
|---|---|---|---|---|
| 4,476,381 A | * | 10/1984 | Rubin | 235/375 |
| 4,847,764 A | * | 7/1989 | Halvorson | 700/231 |
| 5,301,105 A | * | 4/1994 | Cummings, Jr. | 705/2 |
| 5,628,530 A | | 5/1997 | Thornton | |
| 5,659,741 A | * | 8/1997 | Eberhardt | 707/104.1 |
| 5,845,255 A | * | 12/1998 | Mayaud | 705/3 |
| 5,883,370 A | * | 3/1999 | Walker et al. | 235/375 |
| 5,899,998 A | | 5/1999 | McGauley | |
| 5,911,687 A | * | 6/1999 | Sato et al. | 600/300 |
| 5,943,423 A | | 8/1999 | Muftic | |
| 5,974,124 A | | 10/1999 | Schlueter | |
| 5,995,965 A | | 11/1999 | Experton | |
| 6,011,858 A | | 1/2000 | Stock | |
| 6,283,761 B1 | * | 9/2001 | Joao | 434/236 |
| 6,421,650 B1 | * | 7/2002 | Goetz et al. | 705/3 |
| 6,493,427 B1 | * | 12/2002 | Kobylevsky et al. | 379/67.1 |
| 6,539,101 B1 | * | 3/2003 | Black | 382/124 |
| 6,697,783 B1 | * | 2/2004 | Brinkman et al. | 705/3 |
| 2002/0138306 A1 | * | 9/2002 | Sabovich | 705/3 |
| 2002/0173875 A1 | * | 11/2002 | Wallace et al. | 700/242 |
| 2002/0178031 A1 | * | 11/2002 | Sorensen et al. | 705/2 |
| 2003/0216831 A1 | * | 11/2003 | Hart et al. | 700/235 |

OTHER PUBLICATIONS

Ferry, J., "Virtual Doctors on the Horizon in Seattle." The Lancet, vol. 354, Sep. 11, 1999, p. 926.*
S. Morris, "Australian healthcare: a Smart card for a Clever Country", International Journal of Bio-Medical Computing, 40(1995) 101-105, Elsevier Science.
E. Kühnel, "Smart Cards and their Opportunities for Controlling Health Information Systems", International Journal of Bio-Medical Computing, 35(Suppl. 1) (1994) 153-157, Elsevier Science Ireland.

* cited by examiner

*Primary Examiner*—James P. Trammell
*Assistant Examiner*—Martin A Gottschalk
(74) *Attorney, Agent, or Firm*—Howard E. Lebowitz

(57) ABSTRACT

The invention pertains to a healthcare information management system which enables a patient to take possession and control of his healthcare information provided by a plurality of generally unrelated healthcare practitioners and pharmacies, comprising a central database, a portable access device provided to each patient, and a computer system at each health care practitioner and pharmacy. Methods are provided for improved electronic prescription preparation and fulfillment based on comprehensive medical information stored in the system.

14 Claims, 10 Drawing Sheets

SMART HEALTH CARD DOMAINS 900

| | |
|---|---|
| PERSONAL DATA | 901 |
| INSURANCE DATA | 902 |
| EMERGENCY CONTACTS | 903 |
| VITAL DATA | 904 |
| DIAGNOSTIC DATA | 905 |
| MEDICAL DOCTORS | 906 |
| DENTAL DOCTORS | 907 |
| VISION DOCTORS | 908 |
| DOCTOR/HOSPITAL VISITS | 909 |
| HOSPITALIZATION | 910 |
| SURGERY INFORMATION | 911 |
| LAB TESTS REPORT | 912 |
| PHARMACIES | 913 |
| PRESCRIPTIONS | 914 |
| NON-PRESCRIPTION DRUGS | 915 |
| VITAMINS | 916 |
| ALLERGIES | 917 |
| ADVERSE REACTIONS | 918 |
| FITNESS PROFILE | 919 |
| FAMILY PROFILE | 920 |
| DENTAL DATA | 921 |
| VISION DATA | 922 |
| X-RAY DATA | 923 |
| SAMPLE MEDICATION PRESCRIPTIONS | 924 |
| SCHEDULER DATA | 925 |
| Specific Internet / Web Addresses (URL's) | 926 |
| Organ Donor Consent Data | 927 |
| Personal DNA/Genome Data | 928 |

FIG. 9

FIG. 10
READ/WRITE ACCESS TO USERS

| PATIENT | PHYSICIAN | PHARMACY | DESCRIPTION |
|---|---|---|---|
| X | R/W | X | Physician Registration |
| X | X | R/W | Pharmacy Registration |
| R/W | X | X | Patient Registration |
| R/W | R | R | Personal Information |
| R/W | R | X | Emergency Information |
| R/W | R | R | Insurance Information |
| R/W | R/W | R | Health Care Providers Information |
| R/W | R | R/W | Preferred Pharmacy Information |
| R/W | R/W | X | Current Health Conditions |
| R | R/W | X | Physician Observations and Prescriptions |
| R | R | R/W | Pharmacy Prescriptions Fulfillment |

R => Read Only Access
R/W => Read ad Write Access
W => Write Only Access
X => No Access

SECURE ELECTRONIC HEALTHCARE INFORMATION MANAGEMENT PROCESS AND SYSTEM

This application claims the benefit of our prior Provisional Application No. 60/191,023 filed on Mar. 21, 2000, which is hereby included herein by reference.

BACKGROUND OF THE INVENTION

1. Field of the Invention

The invention relates methods and systems for managing healthcare information of medical patients using a central computer database which is accessible to remote clients, portable access devices such as smart cards, and distributed computer systems at medical practitioners, pharmacies, insurers, and other medical providers.

2. Description of the Prior Art

In a large multi-discipline medical clinic setting it is customary to maintain a common database of the patient's medical data which can be accessed by different practitioners who may treat the patient from time to time. The same database may also be used for billing and coordination of insurance benefits. The practice of maintaining a common database has obvious benefits and efficiencies compared to the option of each healthcare provider keeping separate records. One major benefit is that a practitioner providing treatment to a patient can access the patient's entire health record, which may be relevant to the current treatment. A central database is a much more efficient way to provide data than relying on the patient to relate the important information to each practitioner or having all of the practitioners confer with each other. However, few patients are able to rely on a single clinic for all of their healthcare needs, and many patients rely on an assembly of unrelated practitioners for primary medical care, medical specialties, dentistry, eye care, unconventional treatments, pharmaceuticals, and the like.

Most patients must rely on a system where their records are distributed among a number of healthcare providers, physicians, dentists, nurse practitioners, unconventional practitioners, pharmacies, opticians, laboratories, and etc. This creates many opportunities for error. A physician may prescribe drugs which interact adversely with other drugs the patient is being given by another physician, or which are contraindicated for a condition which is being treated by another physician. In an environment where patients are treated by unrelated practitioners, as is often the case, it is likely that errors in prescribing will take place. Even when a single physician is treating a patient, there is room for error in computing the dosage and selecting the proper drug name, for instance among several related drugs with similar names.

Pharmacies can improperly fill a written prescription due to misreading of a handwritten prescription. Due to similarities in the trade names of drugs, even electronic prescriptions are subject to errors.

Another problem is lack of feed back that a prescription has actually been fulfilled by a patient. A doctor who prescribes a medication can only assume that the patient actually secures the prescription, and continues to refill the prescription as required from time to time. In the case of elderly patients, impoverished patients, or the mentally infirm this is not necessarily a good assumption. In the current environment, there is no feed back that a patient ever fills a prescription or continues to refill the prescription for physicians and patients outside of a large integrated clinic setting. Errors due to mismanagement of prescriptions and medications have led to several thousands of lost lives in the United States alone.

Smart cards have been proposed for containing general patient information, emergency contacts, allergies, conditions and the like.

U.S. Pat. No. 5,943,423 teaches use of a smart token system (smart cards) to facilitate secure transactions, including storage and transmittal of patient medical information. U.S. Pat. No. 5,995,965 teaches use of a smart card to access data, such as health data, in remote databases. U.S. Pat. No. 5,899,998 teaches a method and system for maintaining computerized medical records in a distributed system without a central database. U.S. Pat. No. 5,974,124 teaches a method and system for taking patient medical readings, storing them on a smart card, and uploading the data to a primary computer. U.S. Pat. No. 5,628,530 teaches a method and system for tracking the demographics of starter drug samples using smart cards to track the prescriptions. U.S. Pat. No. 6,011,858 teaches a memory card containing a biometric template of a user for security and verification purposes.

There is a need for a healthcare information management system which gives a patient using the services of a variety of generally unrelated healthcare practitioners and providers with control over their health records and the ability to provide comprehensive access to the patient's health records as would occur in a centralized clinic setting to in effect create a virtual medical clinic.

There is a need for methods and systems for improved prescription preparation and fulfillment based on use of a patients comprehensive digital health history which provides verification of proper choice of medication and proper fulfillment of the prescription by a pharmacy.

There is a need for an improved method and system for prescription preparation and fulfillment which provides automatic feedback when a prescription is fulfilled, in order to reduce errors relating to medications.

SUMMARY OF THE INVENTION

The invention involves methods and systems for managing healthcare information of medical patients. An important feature of the methods and systems of the invention is that they provide patients with possession and control of their medical information records and provide the capability to make them available on a selective basis to various healthcare practitioners as needed for efficient treatment while preserving the patients' privacy.

In a large multi-discipline medical clinic setting it is customary to maintain a common database of the patient's medical data which can be accessed by different practitioners who may treat the patient from time to time. The same database may also be used for billing and coordination of insurance benefits. The practice of maintaining a common database has obvious benefits and efficiencies compared to the option of each healthcare provider keeping separate records. One major benefit is that a practitioner providing treatment to a patient can access the patient's entire health record, which may be relevant to the current treatment. A central database is a much more efficient way to provide data than relying on the patient to relate the important information to each practitioner or having all of the practitioners confer with each other. However, few patients are able to rely on a single clinic for all of their healthcare needs, and many patients rely on an assembly of unrelated practitioners for primary medical care, medical specialties, dentistry, eye care, unconventional treatments, pharmaceuticals, and the like.

The instant invention provides methods and systems which allow a patient to assemble a unique virtual medical clinic, where the various practitioners and providers are joined together by the methods and systems provided, to share information.

An embodiment of the invention is a healthcare information management system which would serve a group of medical patients, healthcare practitioners (physicians, dentists, chiropractors, nurses, herbalists, pharmacies, etc.), and other associated parties such as hospitals and insurance providers. The system provides for continuously updated healthcare history of patients in a central database and on portable access devices, which are preferably smart cards carried by patients. Use of the system, provides the benefits and conveniences of a common database maintained by a "rear" clinic. One significant example is a superior method information management with respect to medications and processing of prescriptions for medications.

A healthcare information management system comprises a central database system which is accessible to remote computer systems; a plurality of remote computer systems located at healthcare practitioners, pharmacies, patient members, and other parties such as insurance providers; and a plurality of smart cards, at least one smart card for each patient.

The central database system comprises a network server for communicating with the various remote computer systems. Communication may be over the Internet, other networks, telephone, or other suitable means. The central database system further comprises a central database and database server for storing and retrieving information about medical patients, medical practitioners, pharmacies and insurance providers. In particular, the database contains health histories of the medical patients and records of treatment by medical practitioners including records of medical prescriptions issued by medical practitioners and fulfillment of medical prescriptions by pharmacies. The network server is operated by software which allows communication with the remote computer systems and transfers information to and from the database server for maintenance of the database and for providing patient specific information to medical practitioners, pharmacies, medical patients, insurance providers, and other authorized parties. The central database system further comprises an application server which provides software which assists medical practitioners in prescribing medications and assists pharmacies in confirming the suitability of a medication for the patient.

The health care information management system further includes a plurality of portable access devices, preferably smart cards, which are provided to patients. The smart cards include data domains which comprise the patients demographic, personal, and emergency information, medications taken, health history, records of recent medical treatment, and particularly prescriptions for medicines prescribed by medical practitioners, and a record of fulfillment of those prescriptions by pharmacies. The data domains are secured so that different domains are accessible only by authorized parties, with different access privileges.

The health care information management system includes a plurality of computer systems located at healthcare practitioners, each system comprising at least one computer and peripherals. Each system may be either a single computer or a local network in a healthcare office. The healthcare practitioner's computer system includes a device reader capable of reading from and writing to the portable access device under control of the healthcare practitioner's computer system, at least one external communication device, and preferably a biometric device for making a biometric measurement to verify the identity of the healthcare practitioner. The practitioner's computer system is preferably capable of connection to the Internet and as a minimum is capable of sending and receiving electronic mail. The software operating the practitioner's computer system contains functionality which enables the system to read a patient's medical history from the patient's smart card, and to write a report of treatment to the smart card, and if required to write one or more medical prescriptions for fulfillment at a pharmacy in a format which can be read by the computer system at a pharmacy and containing a digital signature identifying the practitioner. The software preferably provides functionality for authenticating the identity of the user, preferably by comparing a biometric measurement to a reference, prior to accessing the smart card and granting access to the card based on the rights assigned to the particular user. The practitioner's computer system optionally contains software for assisting the practitioner with prescribing medications based on a patient's health history information and properties of the various medications. The software comprises functionality to contemporaneously send an electronic message containing a copy of the prescription to the Central database system whenever a prescription is written to a patients smart card, and preferably to send an electronic message containing the prescription to the patients preferred pharmacy (address read from the smart card). The software also has the capability for affixing the physicians electronic signature to an email prescription sent to the pharmacy so that the email could be used as a valid prescription for a patient without a smart card.

The health care information management system further includes a plurality of computer systems at pharmacies. These systems comprise the same components as a healthcare practitioner's system, though with somewhat different software, and a scanner for reading a code from a medicine container. The code is preferably a universal bar code which identifies the drug contents according to a predefined standard. The software operating the pharmacy computer system enables it to read a prescription from a patient's smart card. The software also allow the pharmacy computer system to recognize digitally signed "electronic prescriptions" received as e-mail for a patient without a smart card. The drug is then secured and an identifying code is scanned from the container. The software enables the computer system to compare the prescribed drug with the scanned result and verifies that the prescription is correct. If verified, the prescription is filled and the smart card is updated to indicate that the prescription has been filled. If more than one refill was prescribed, the refills remaining are decremented, and the card is electronically signed by the pharmacy. The software is programmed such that the pharmacy computer automatically sends electronic messages to the prescribing medical practitioner and the central database confirming that the prescription has been fulfilled when the smart card is updated. Electronic messages are also sent to the practitioner and to the central database system when the pharmacist indicates that an electronic prescription, received by e-mail, has been filled.

The health care information management system further includes a plurality of optional patient computer systems. Patient systems comprise a computer, smart card reader, and preferably a biometric measurement device and an Internet connection. The patient system comprises software to allow a patient to input health history, personal data, emergency contacts, health practitioners, pharmacies, insurance providers, and others. The software allows a patient to read but not modify records of treatment or prescriptions.

Most of the writings to the card are in accordance with a predetermined format and are encrypted so that they can only be accessed by members who have authenticated themselves to the system. The exception is certain identification, medical summary, and emergency contact information which could be left accessible to anyone with a proper card reader.

The pharmacy computer systems, healthcare practitioner computer systems, and patient computer systems may be operated in a stand alone mode as described above, or a connected mode where they are connected to the central database over a network, such as the Internet, or a direct phone connection, satellite transmission or other connection means. When the local computer systems are operated in the mode where they are connected to the central database system, both the smart card and central database are simultaneously updated with the new information when the smart card is updated as described above. Since the smart card can also be used with the local computer in the standalone mode it is possible for the smart card to have more recent data than is present on the central database. For this reason, the central database is updated, and the smart card and central database synchronized, whenever one of the local computer systems is run in the mode where it is connected to the central database and the smart card is written to by the local computer system.

The ability to operate in both modes is a critical feature of the invention. The smart card has the advantage of availability and simplicity. However, the smart card has limited storage capacity so it will not always be able to hold an entire health file which will reside on the central database. On the other hand, practitioners and pharmacies are likely to serve a mixture of patients, of which only some will be members of the health information management systems. It, therefore, will not always be convenient for practitioners to establish contact with the central database when serving a patient.

The healthcare information management system may be used to provide patients with the capability of assembling a virtual healthcare clinic by enrolling healthcare practitioners, pharmacies, and patients into a healthcare information management system equipped as above. Patients could choose enrolled practitioners and provide their smart card when they seek treatment. A practitioner would have access to the patients medical history and would add a record of treatment and possibly a prescription. The patient could take the card to a pharmacy to get a prescription fulfilled. The pharmacy system would read the prescription, choose and verify the prescription electronically, fulfill the prescription, and electronically notify the prescribing practitioner that the prescription was fulfilled.

Carrying the prescription on the smart card is particularly convenient for a patient, since the prescription can be accessed by any enrolled pharmacy for issuance of refills, without the need to contact the prescribing practitioner or the original pharmacy. As seen in the embodiment below, the system generates automatic notification to the prescribing practitioner when a prescription is being fulfilled, so that there is a record that the patient is complying with the prescribed regimen.

Another embodiment of the invention is a reliable, secure, closed loop method of managing a medical prescription issued to a patient, comprising the following acts:

1. A healthcare practitioner starts up the software on the practitioners computer system and authenticates to the health information system software, preferably using a biometric measurement, such as a fingerprint identification.
2. The medical practitioner chooses a prescription for a patient and enters it on the prescription form. As part of the procedure, the practitioners electronic signature is entered onto the prescription.
3. The prescription is written to the smart card.
4. The practitioner's computer sends an electronic copy of the prescription to the central data base and to the patient's preferred pharmacy's computer system (whose address it reads from the smart card) contemporaneously with writing the prescription to the smart card.
5. The patient presents the smart card to a pharmacy, which may or may not be the preferred pharmacy.
6. A pharmacist at the pharmacy accesses the pharmacy computer system and authenticates to the health information system software. The smart card is read and the medication is identified. Alternatively, the medication is identified from an "electronic prescription" in the form of a digitally signed e-mail. A container of the medication is procured and the bar code is scanned. The computer system identifies the medicine corresponding to the bar code and compares it to the medicine prescribed. If it is the correct medication the pharmacist dispenses the drug, and the pharmacy computer system updates the smart card to indicate that the prescription has been dispensed. The refill counter is decremented and the card is signed with the pharmacy's electronic signature.
7. Contemporaneously with updating the smart card, the pharmacy computer system sends electronic messages to the healthcare practitioner's computer system and to the central database indicating that the prescription has been fulfilled.

An object of the invention is to provide methods and systems which allow patients utilizing a variety of generally unrelated healthcare practitioners and pharmacies to have possession and control of their medical records and to make their records available to their healthcare providers in a prompt, reliable and secure manner to improve the quality of their healthcare treatment.

A further object of the invention is to provide methods and systems for improved computer assisted preparation and fulfillment of medical prescriptions based on the patient's digital health records and verification that the proper medication has been chosen by a practitioner and fulfilled by a pharmacy.

A still further object of the invention is an improved electronic medical prescription method and system which provides feedback that a prescription has been fulfilled.

BRIEF DESCRIPTION OF THE DRAWINGS

These and other features, aspects and advantages of the present invention will become better understood with regard to the following description, appended claims and accompanying drawings, where:

FIG. 9 show a typical domain allocation of a smart card.

FIG. 10 is a table of a typical read/write allocation of files to members.

DESCRIPTION OF THE PREFERRED EMBODIMENTS

The invention pertains to a healthcare information management system which can be used to manage the composite medical information about a patient into a single virtual medical clinic notwithstanding the fact that the patient may utilize the services of a number of different healthcare practitioners and service providers who are generally unrelated except for enrollment in the healthcare information management system. A patient benefits by having possession and control over his medical healthcare records which he can selectively make available to healthcare practitioners. A patient also benefits from improved quality control in his healthcare treatment as is manifested by a closed loop medical prescription method which includes automatic electronic verification that the medicine physically dispensed by the pharmacist is the one prescribed by the practitioner, and feedback to a practitioner that a prescription given to a patient has actually been fulfilled.

Figure 1:
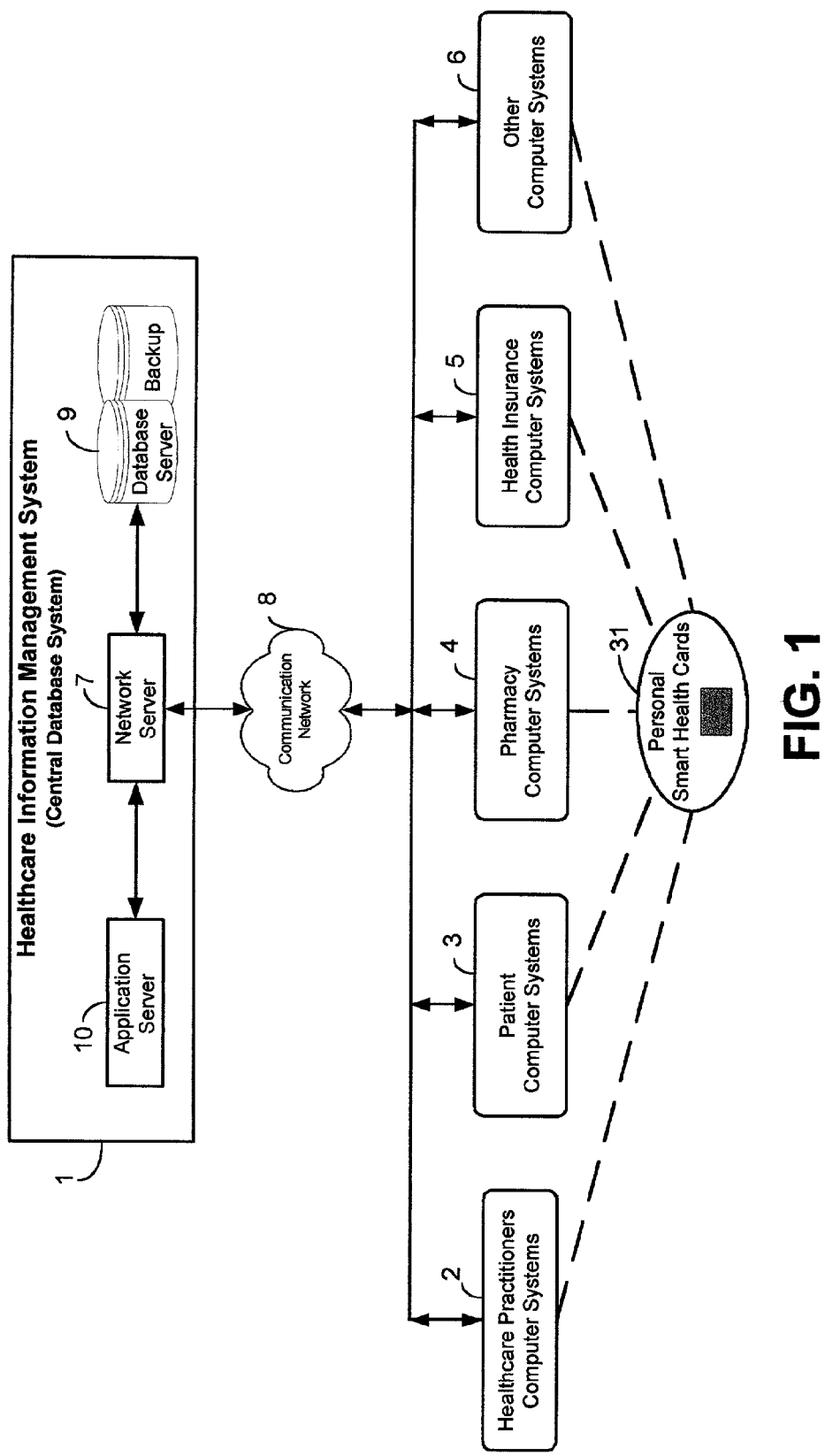
FIG. 1 is an overview block diagram of a healthcare information management system.

Referring to FIG. 1, the healthcare information system comprises a central database system 1, a plurality of portable access devices 31, preferably smart cards, one for each enrolled patient, and a plurality of local computer systems for accessing the smart cards and the central database by healthcare practitioners 2, pharmacies 4, patients 3, and optionally others 5 and 6. Each class of local computer system has particular hardware and software to serve the functions of that class of user. The healthcare practitioner's systems, pharmacy systems, and patient systems have appropriate read/write units to access the cards, and software operating their computer systems to access data on the cards which is encrypted and written according to a particular format. The components in FIG. 1 are shown with only one member of each type for convenience, however it should be understood that there are many local servers and smart cards, and preferably one central database system.

The central database system, the local computer systems and the smart cards work together to provide the healthcare information system. The central database system contains a single database which is the ultimate archive of member patients' health records. It contains software for managing the database and for obtaining data from the local computer systems and presenting data to the local databases. A patient's healthcare practitioners, pharmacists, the patient, and other authorized parties such as insurance companies, may access that portion of a patient's health data that they are authorized to access through a local computer system by an external connection, generally a network such as the Internet. A patient's general health history and records of recent treatments by physicians, nurses, dentists, and other practitioners, prescriptions, insurance status, and other relevant information such as demographic data and emergency contacts are also contained on the patients smart card. Because of the size of a smart card, all of a patient's information will not generally fit on the health card. Each local computer will have the capability of completing a transaction using the smart card alone in a stand alone mode or the smart card in combination with the central database system in a combination mode. Whenever a smart card is accessed as part of a transaction in the combination mode the new data is provided to both the central database and to the smart card; also at each access to the smart card the contents of the smart card and the central database are synchronized—new data placed on the smart card in standalone mode is uploaded to the central database and new data which has been added to the database about a patient (such as insurance status—payments, whether deductibles have been met or plan maximums have been reached) are downloaded to the hard card. Files which have been updated are flagged. When a smart card is full the oldest, flagged files will be overwritten, so that the most recent data will remain on the card.

The ability to operate in both standalone and connected modes is a critical feature of the invention. The smart card has the advantage of availability and simplicity. However, the smart card has limited storage capacity so it will not be able to hold an entire health file which will reside on the smart card. On the other hand, practitioners and pharmacies are likely to serve a mixture of patients, of which only some will be members of the health information management systems. It, therefore, will not always be convenient for practitioners to establish contact with the central database when serving a patient.

The structure of the system, leads to unexpected benefits. One benefit is a closed loop method for preventing errors in dispensing prescription medications. The system provides software to aid in prescribing medications during the prescription process which can be based on the health history and other data which is available in digital form, transmission of the prescription via the smart cards reduces the chances of error in reading the prescription and allows for automatic verification that the correct medication is being dispensed by a computerized process of comparing the electronic prescription with identification scanned from the medicine bottle. Electronic confirmations are exchanged among the central database, a prescribing practitioner and the pharmacy confirming that a prescription is on the way and has indeed been fulfilled. Therefore all major points of error are automatically eliminated.

Figure 8:
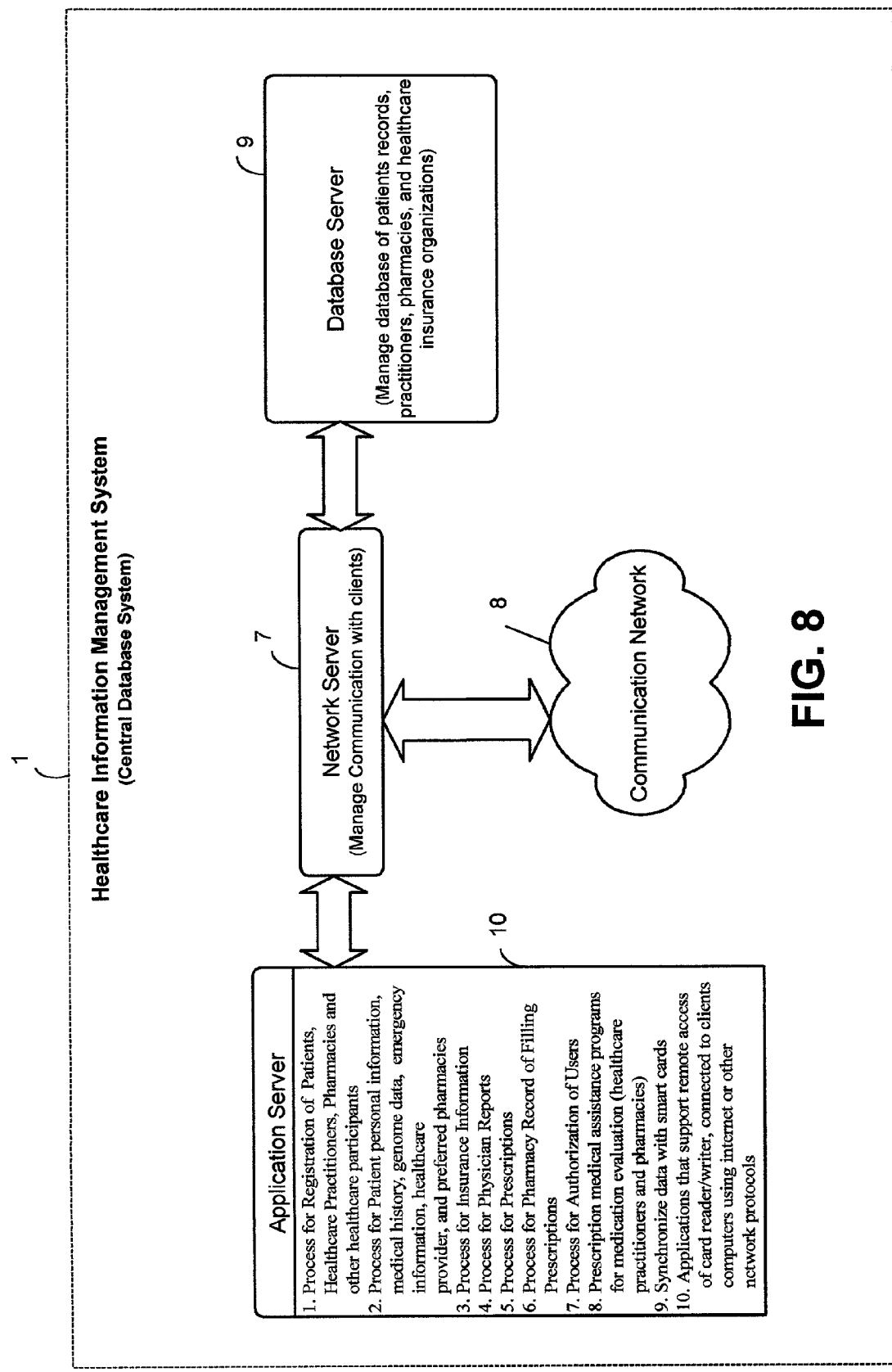
FIG. 8 is a block diagram of the central database system.

A central database system is shown in FIG. 8. The central database system is shown as three servers a application server, a network server and a database server. The designations of the servers and their functions is typical but not limiting to the invention. In particular there may be many servers of each type or the functionality may be distributed differently among the servers than what is indicated, in ways which will be well known to those skilled in the art. Servers are preferably standard machines available from HP, Sun, etc. UNIX or Microsoft Windows are some of the operating systems that can be used. Servers should have adequate disk space and memory and high speed network connection.

The Application server contains software for displaying forms which will be sent out over the network to local computer systems to collect data from the users, and to send data to be displayed on the local systems. A preferred format is world wide web based interface for the application pages, with routines to query the local systems or the database server and make indicated comparisons and choices. Preferably SQL database tables are used for data storage. The pages and routines comprise the following:

1. Sign on.
    a) Log in and authentication of existing users, followed by access to authorized files. Registration of new patients, healthcare practitioners, pharmacies, and other authorized users.

2. For a patient
    a) Choice of whether to access data from the central data base or the smart card.
    b) Pages for input and review including registration information, personal information, emergency contact information, insurance information, healthcare providers, preferred pharmacies, current health issues, treatment records (read only) from healthcare providers, prescription records (read only access).
c) Choice of whether to update central database and synchronize central database and smart card.

3. For healthcare provider.
   a) Choice of patient and choice whether to access data from the central data base or the smart card.
   b) Read only access to patient provided input data and data by other parties including insurance providers,
   c) Forms to input new records of treatment and prescriptions and ability to review prior records.
   d) Optional access to a knowledge base for computer based assistance in prescribing, comprising drug selection assistance based on the entered diagnosis, calculation of dosage based on patient age, weight, history, and other medications used, dosage timing, drug interactions checker, identification of side effects and precautions, and the like.
   e) Choice of whether to update central database and synchronize central database and smart card. Prescriptions are electronically signed at the healthcare provider's local computer system during updating.
   f) Send electronic message to preferred pharmacy and central data base if prescription written.

4. For a pharmacy
   a) Choice of patient and choice whether to access data from the central data base or the smart card.
   b) Read only access to patient provided input data.
   c) Access to prescriptions outstanding.
   d) Ability to receive scan code from a medication and software to compare whether it is the drug prescribed as read from the electronic prescription.
   e) Optional access to a knowledge base for computer based assistance in checking the prescribed drug for interactions with other medications that the patient is taking as indicated in the medical history, contra indications which may be present based on the patients medical history, and adverse side effects to warn the patient about.
   f) Choice of whether to update central database and synchronize central database and smart card. Prescriptions electronically signed at the pharmacy computer system during updating and the refills counter is decremented based on the quantity of medication dispensed.

5. Other Users—Optional
   a) Pages may be provided for inputs from insurance providers, indicating status of coverage, co-payment to be collected, patient paid deductibles and whether the deductibles have been met.
   b) Pages may be provided for inputs from providers such as laboratories.

6. General Purpose functions
   a) Software routines to interact with the network server and database server.
   b) Software routines to interact with the local client computer systems to synchronize the contents of the smart card and the central data base. The database and smart card may contain different information due to use of the card in one of the local computer systems in the standalone mode (without connection to the central database system) in which case the card has data which the central system does no possess. Alternatively, there may be input from miscellaneous users, such as insurance providers, who communicate with the central database directly without the smart card, in which case the central database has information which is not on the card. Files on the central database and on the smart cards are flagged when they have been transferred. During synchronization, unflagged files are exchanged.

Various data pages are assigned different read/write status to different users. An example of an assignment is shown in FIG. 10.

The database server contains the central database of healthcare data, and routines to access the data, input new data, edit and delete data and all the normal database management functions, which are well known in the art. The database server is preferably continuously backed up for integrity of the data.

The network server performs the usual functions of presenting to the communications network, preferably the public Internet or a similar network. Communication over the network preferably uses an encryption method such as secure sockets layer (SSL) or transport layer security (TSL) to insure secure communication between the central database and the local client computers. A higher level of security can be obtained using virtual private networking (VPN) technology over the Internet or other similar network. All of these may be implemented by routines and techniques which are readily available and well known to those skilled in the art.

Figure 2:
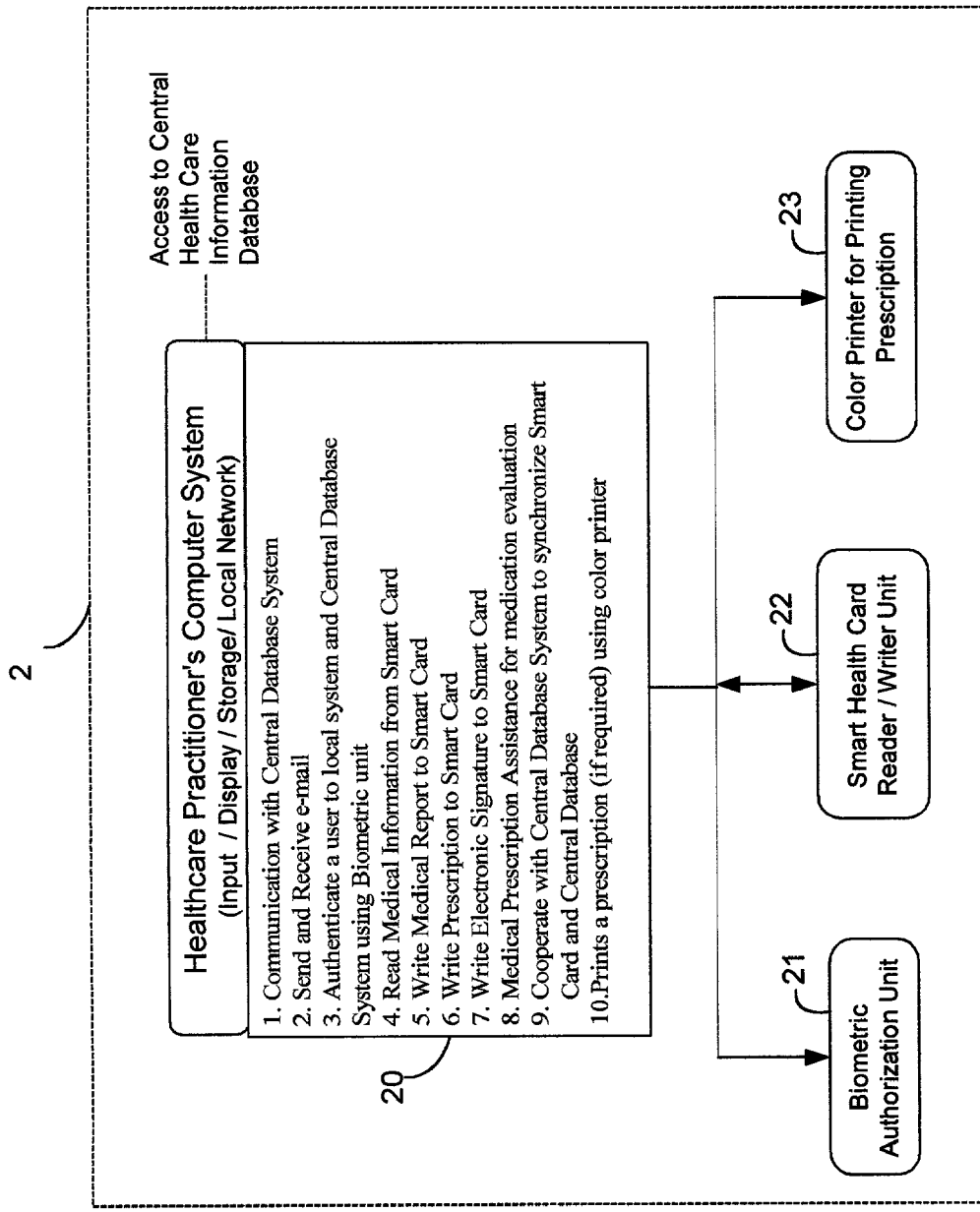
FIG. 2 is a block diagram of a typical healthcare practitioner's computer system.

FIG. 2 show a block diagram of a computer system 2 for a healthcare practitioner. The system comprises a computer 20 which may be a stand alone computer or may be networked to an office practice or clinic network depending on the circumstances. The computer system has the usual input, display, and storage devices as well a smart card reader/writer 22. The computer system preferably contains a biometric authentication/verification unit 21 such as a fingerprint, iris or voice verification unit for authentication of users. Alternatively, a smart card which can be used in the smart card reader/writer peripheral 22 may be used configured to accept a password and allowing only a limited number of attempts for access may be used for authentication or a similarly functioning software device which is located on the computer hard disc, such as a software smart card. One preferred computer system is an industry standard personal computer, with an Pentium II dual-CPU processor, 256 KB of RAM, 20 GB hard drive, 56K modem and typical I/O devices. A suitable smart card reader/writer is the GEMPLUS GCR 410 as manufactured by GEMPLUS Corp. coupled to the computer with USB or serial interface. The system is preferably connected to the Internet or another network through which it can access the central database system, and as a minimum be able to send and receive electronic mail through a public network, preferably the Internet. Of course, other similar computer and smart card devices are also acceptable.

The software on the medical practitioner's system will include functionality to operate as a client to the central data base system, to send and receive data as indicated previously in the description of the central database system, for a healthcare practitioner. The healthcare practitioner computer system will also include on board the capability to perform the functions in a stand alone mode, where it is not connected to the central database system at all and relies solely on the patients smart card to provide information about the patient, to input a report of treatment and to write an electronic prescription to the smart card. A preferred interface in either mode is a world wide web browser such as Microsoft Internet Explorer 5.0. The healthcare practitioner system will be equipped to operate the authentication device and authenticate authorized users to the system as well as to the central database system if connected. The healthcare practitioner computer system software preferably includes the capability to sign an electronic signature of user which is capable of being of being recognized by other members of the healthcare information management system, preferably with a PKI system with a digital certificate supplied by a common certifying authority and requiring authentication of the user for activation. The healthcare practitioner's computer system software contains the drivers to write to the smart cards in a predefined format used throughout the healthcare information management system, to encrypt and decrypt the data written to or read from a smart card. The drivers on the healthcare providers computer system are used to access the smart card in both standalone modes or when used as a client to the central database. The software on the healthcare practitioner's computer system interacts with the central database system to synchronize the smart card and the central database whenever the smart card is written to while practitioner's system is operating in the client mode to the central database system.

Figure 3:
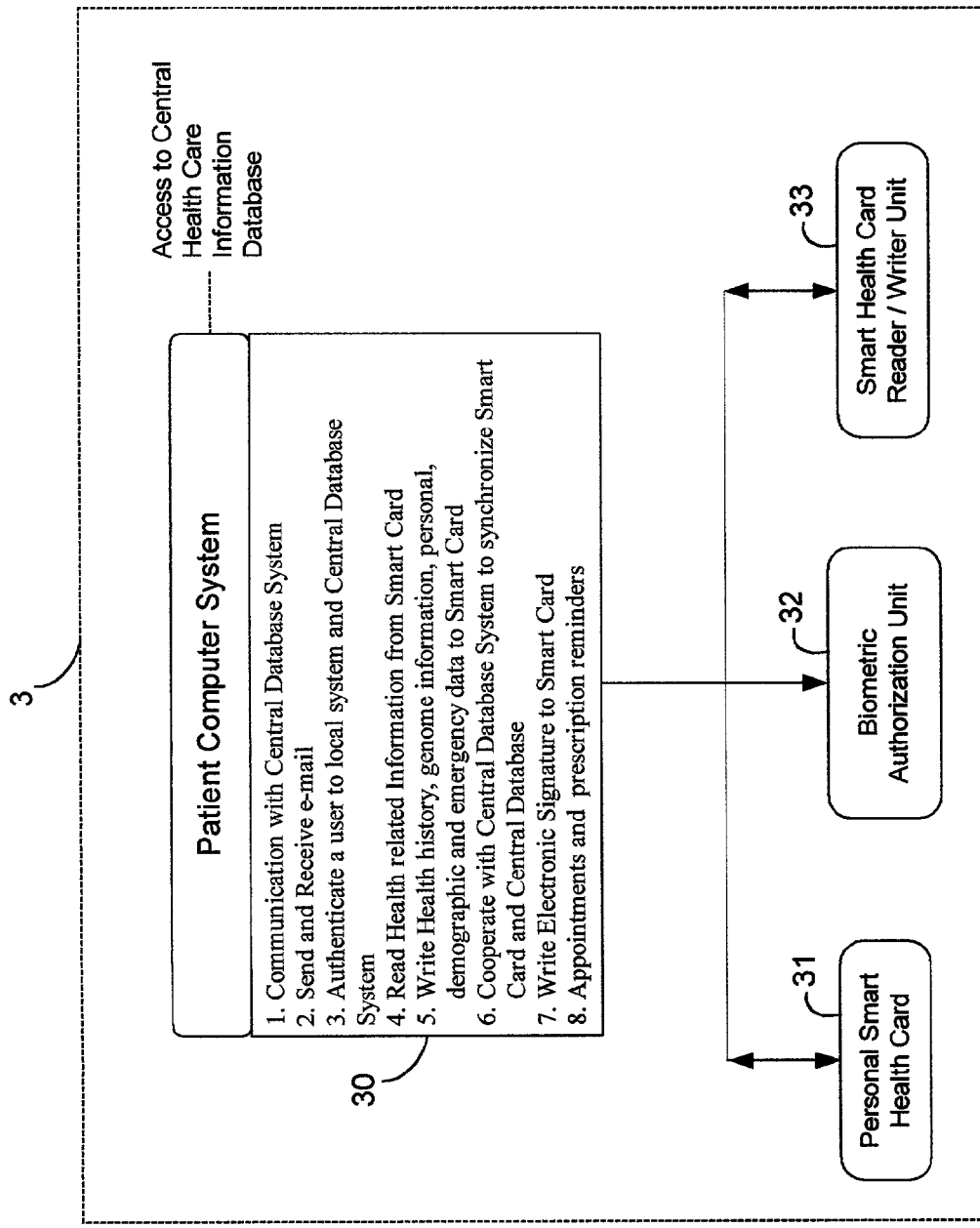
FIG. 3 is a block diagram of a typical patient's computer system.

A patient's computer system 3 is shown in FIG. 3 comprising a patient computer 30, a person smart health card 31, an authentication unit 32, and a smart card reader/writer 33. The computer 30, the authentication unit 32, and the smart card reader writer 33, are equivalent to the comparable units in the healthcare practitioner's system.

A portable access device is a small device, preferably small enough to fit into a patient's wallet. A preferred device is smart card 31, but the invention could be implemented for a larger device such as a portable assistant, or the like. A smart card is generally a small plastic card which is approximately credit card size. The preferred type of smart card is a microprocessor card which contains an integrated circuit chip equivalent to a microprocessor, random access memory, read only memory and non-volatile memory. Smart cards also have a cryptographic co-processor that can process asymmetric cryptographic algorithms. Smart cards have an input/output port which can be either contact type (usually a small gold plate on the front) or contactless (use an electronic microchip and antenna embedded inside). Either type is acceptable for the invention or a combination of the two. Input/output is accomplished using a reader/writer.

A preferred smart card is an ISO 7816 card which is PC/SC work group compliant. A suitable card is manufactured by GEMPLUS Corp. with the following specifications: ATMEL Chip AT9) SC3232C, High Speed 8 bit RISC AVR (MCU), Hardware Crypto Co-processor, 32 Kbytes Flash Program Memory, 32 Kbytes EEPROM Data Memory, 1 Kbyte SRAM Data Memory, Microsoft Windows for Smart Card operating system. The smart card can be programmed using Visual Basic program, configured using the Microsoft Windows for Smart Card Tool.

The smart card devices may be configured to require entry of a PIN to access the card, and to lock a card after a predetermined number of incorrect tries. This is a powerful security feature for a patient since any use of the card must begin with access expressly granted by the patient. This same feature, would preclude access to the card to the card by potential out of system helpers in an emergency situation. The choice is an option in the health information management system.

The data on a smart card can be partitioned into domains as illustrated in FIG. 9, and access to domains is individually restricted to different users or classes of users, for instance physicians, dentists, pharmacies, patients, opticians, etc., as shown in FIG. 10.

The software on the patient's computer system will include functionality to operate as a client to the central data base system, to send and receive data as indicated previously in the description of the central database system, for a patient. The patient computer system will also include on board the capability to perform the functions in a stand alone mode, where it is not connected to the central database system at all and relies solely on the smart card. A preferred interface in either mode is a world wide web browser such as Microsoft Internet Explorer 5.0. The system will be equipped to operate the authentication device and authenticate the patient to the system as well as to the central database system if connected. The patients computer system software contains the drivers to write to the smart cards in a predefined format used throughout the healthcare information management system, to encrypt and decrypt the data written to or read from a smart card. The drivers on the healthcare providers computer system are used to access the smart card in both standalone modes or when used as a client to the central database. The software on the patient's computer system interacts with the central database system to synchronize the smart card and the central database whenever the smart card is written to while practitioner's system is operating in the client mode to the central database system.

Figure 4:
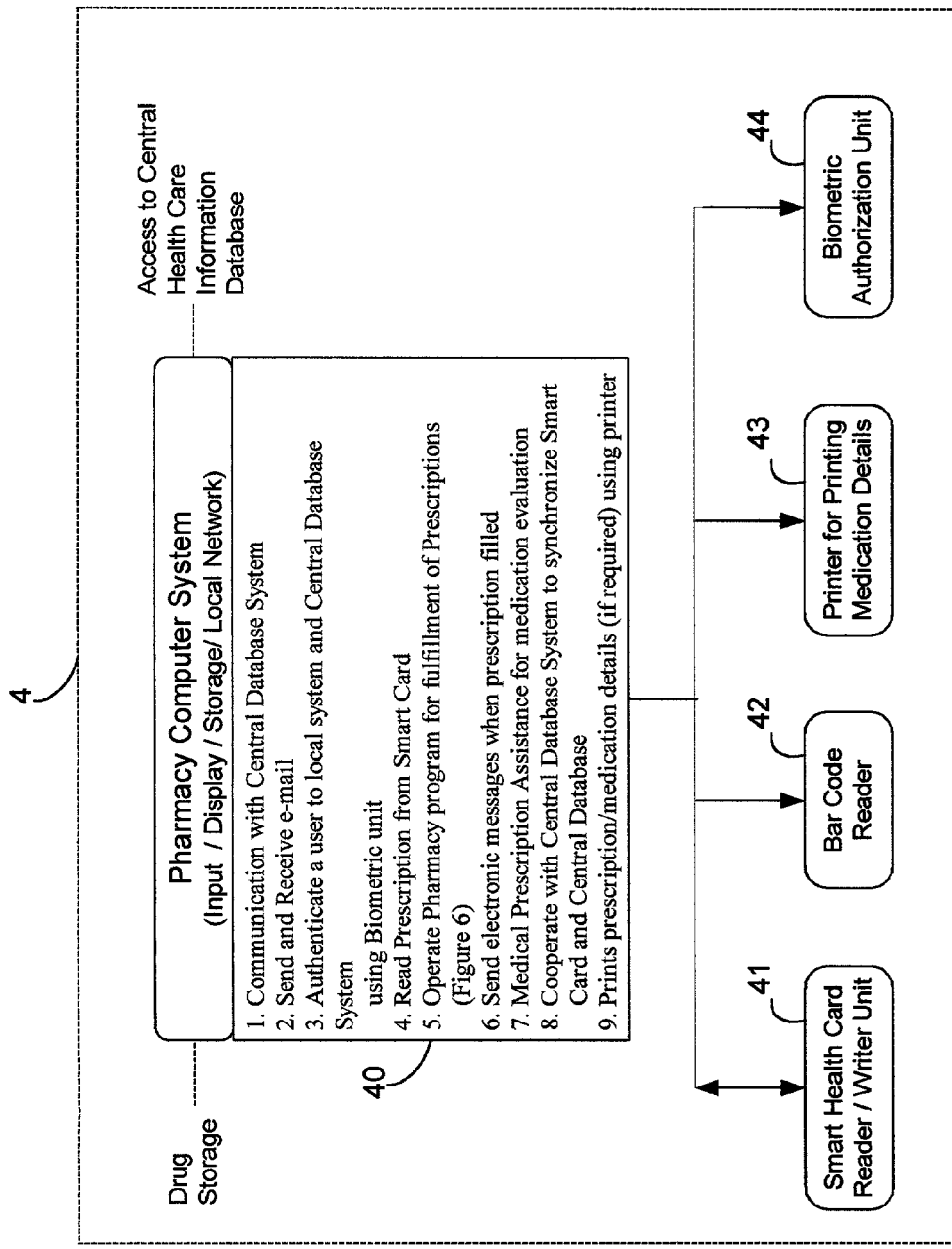
FIG. 4 is a block diagram of a typical pharmacy's computer system.

FIG. 4 shows a block diagram of a pharmacy computer system 4, comprising a label scanner, preferably a bar code reader 42, in addition to the components which would be found on a heath care practitioner's system. The pharmacy computer system is otherwise similar to a health practitioner's system. The software on the pharmacy computer system will include functionality to operate as a client to the central data base system, to send and receive data as indicated previously in the description of the central database system, for a pharmacy. The pharmacy computer system will also include on board the capability to perform the functions in a stand alone mode, where it is not connected to the central database system at all and relies solely on the patients smart card to provide information about the patient, to read an electronic prescription, and to write a confirmation that a prescription has been fulfilled and decrement the refill counter. A preferred interface in either mode is a world wide web browser such as Microsoft Internet Explorer 5.0. The pharmacy computer system will be equipped to operate the authentication device and authenticate authorized users to the system as well as to the central database system if connected. The pharmacy computer system software preferably includes the capability to sign an electronic signature of user which is capable of being recognized by other members of the healthcare information management system, preferably with a PKI system with a digital certificate supplied by a common certifying authority and requiring authentication of the user for activation. The pharmacy computer system software contains the drivers to write to the smart cards in a predefined format used throughout the healthcare information management system, to encrypt and decrypt the data written to or read from a smart card. The drivers on the pharmacy computer system are used to access the smart card in both standalone modes or when used as a client to the central database. The software on the healthcare practitioner's computer system interacts with the central database system to synchronize the smart card and the central database whenever the smart card is written to while practitioner's system is operating in the client mode to the central database system.

The pharmacy software additionally contains drivers to operate the scanner, preferably a bar code scanner. Most drugs contain a bar code label which uniquely identifies the drug. When the prescription filling option is started the program reads a prescription, identifies the medicine prescribed and stores that medicine in a memory. It also causes the label to be read by the scanner and reads a label into a second computer memory. The medicine corresponding to the contents of the second memory is identified from a database and it is verified that the medicine is indeed the one prescribed. In the alternative, if a match cannot be made the pharmacist is notified of the discrepancy and may resolve the matter. Manual input of the drug name is also possible as an alternative. When a prescription is verified and fulfilled, that fact will be entered on the prescription form and written to the smart card. The refills counter, if any, will be decremented. Electronic messages are sent approximately at the same time to the prescribing practitioner and to the central database system confirming that the prescription has been fulfilled.

The major members of a healthcare information system are healthcare practitioners, pharmacies, and patients. In a preferred option of the healthcare information system, insurance providers would also have access to the system. Generally a patient's interaction with an insurance provider is indirect, therefore an insurance provider does not need access to a patient's smart card, but could update patients' files on the central database, such as confirmation of coverage, deductibles, maximums, etc. The information would be available to a practitioner or pharmacy by contacting the central database. The data inputted by an insurance provider and present on the central database would be synchronized with the card each time the card is written to in the combination mode when in use by a practitioner, pharmacy or patient computer system, and would then also be available for use by practitioners, pharmacies, and patients in the standalone mode of operation. In this way, the smart card would serve as an advanced form of insurance card, which would confirm current coverage, and assure collection of deductibles and co-payments. Functionality is optionally added to directly generate reimbursement requests from the practitioner's report of treatment which contains the procedure codes performed by the practitioner. The reimbursement would be calculated from the procedure codes and the reimbursement per procedure taken from a file applicable to the patient's insurance carrier. The request for reimbursement is electronically signed and forwarded electronically to the insurance carrier. A similar procedure would be followed for reimbursement of the pharmacy based on the record of fulfilled prescription.

Another option is to provide access to opticians and other suppliers of healthcare devices with access to read non-drug prescriptions for eye-glasses, contact lenses, orthopedic appliance and the like. Such providers are provided with a computer system similar to that in a pharmacy, but granted more limited access to the patients' data. For instance only the data pertaining to eye treatment.

The healthcare information system is assembled by loading the software onto the database management hardware and connecting the system to a network preferably the Internet and providing the functionality described in a manner which is well known to those skilled in the art.

The local computer systems are similarly set up by loading the software onto either a single purpose computer set up for use with the healthcare information management system or as an application program on a multi-purpose computer system. The local system programs will generally be combined into a single program and the functions would be accessed as menu options in a manner well known in the art. While there are numerous functions implemented by software, each individually is well described by its function and could be readily coded by one skilled in the art.

A healthcare information management system is created by enrolling patient members, healthcare providers, pharmacies, insurance companies and other members by obtaining required information and providing patients with smart cards, and patients, practitioners and pharmacies with computer systems or software to operate their existing systems.

Figure 5:
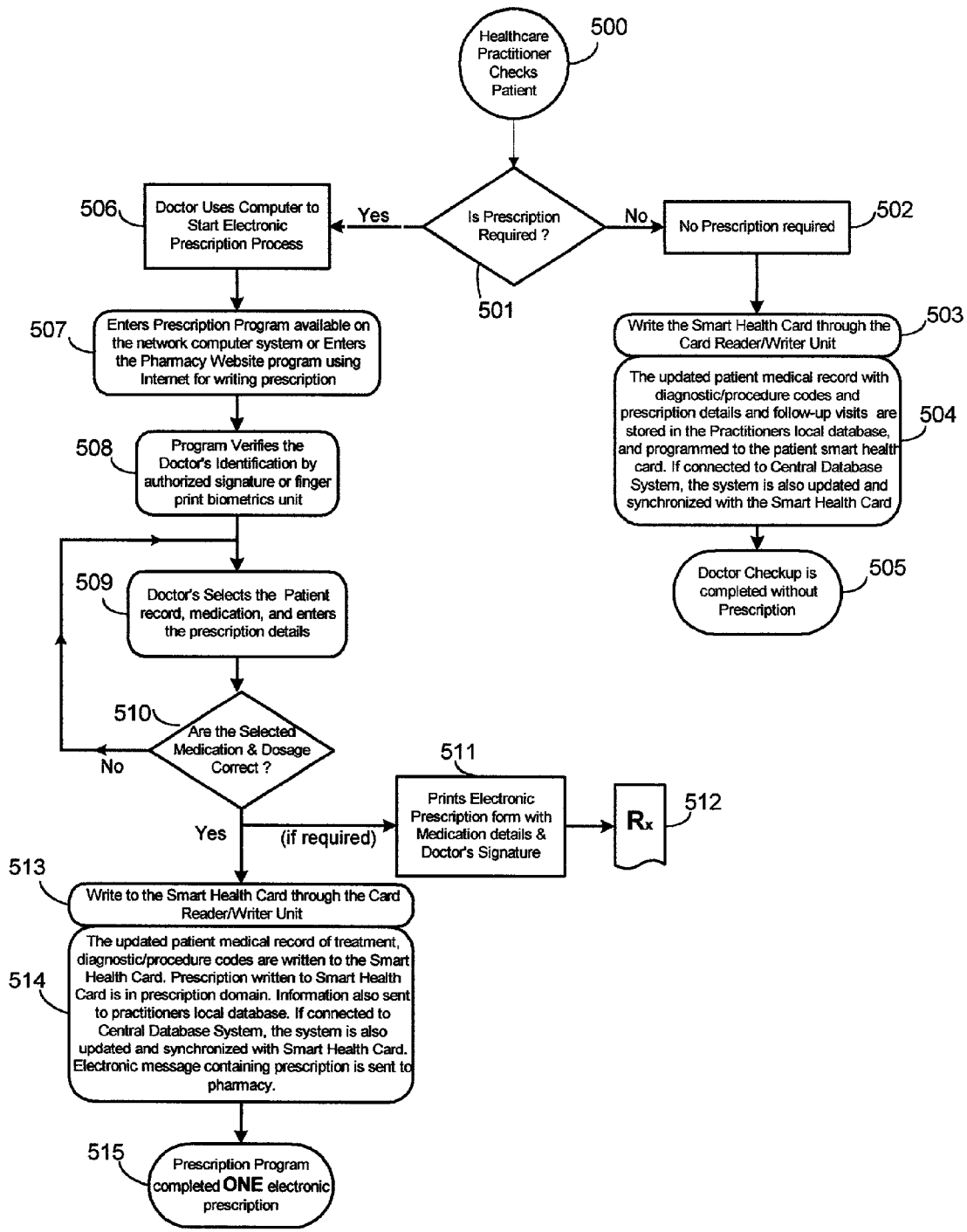
FIG. 5 is a flow chart of the use of the system by a healthcare practitioner.

FIG. 5 demonstrates a procedure using the system in a healthcare practitioners office, here a physician. The physician starts the program in step 500. The program asks whether a prescription is required 501. If no prescription is required 502, the physician authenticates to the system with a fingerprint biometric unit (step not shown) and if the authentication is successful inserts the patient's smart card in the card reader 503. The physician fills out an on screen form inputting relevant details of the treatment, diagnosis, treatment codes, and scheduling the next visit. When the form is completed it is saved. The information on the page is written to the smart card and if the program is run in the connected mode, simultaneously to the central database system. In the latter case, the smart card and central database are synchronized 504.

If a prescription is required, the physician starts the prescription program 506 and 507. The physician authenticates to the system (and central database if in the combined mode) 508 using a biometric unit and the input is compared to the data on file. If authenticated, the physician is prompted to select the correct patient record (if in combined mode), chooses a medication and enters the prescription details into the computer prescription form 509. The physician then optionally uses an online assistance module 510 which checks the prescription and dose based on the patient's health profile and the entered prescription, based on a knowledge base of drug properties and interactions. If the prescription is inappropriate suggestions are made and the program recycles to the entry page (or allows the physician to override and proceed). The physician can optionally print a written prescription. Once satisfied with the prescription, the card is placed in the writing unit and the physician is prompted to input relevant details of the treatment, diagnosis, treatment codes, and scheduling the next visit. The prescription and treatment information is written to the smart card and if the program is run in the connected mode, simultaneously to the central database system. In the latter case, the smart card and central database are synchronized when the card is written to 514. The prescription is electronically signed with the physician's signature before the prescription is recorded. An electronic message is sent to the patient's preferred pharmacy (read from the smart card).

Figure 6:
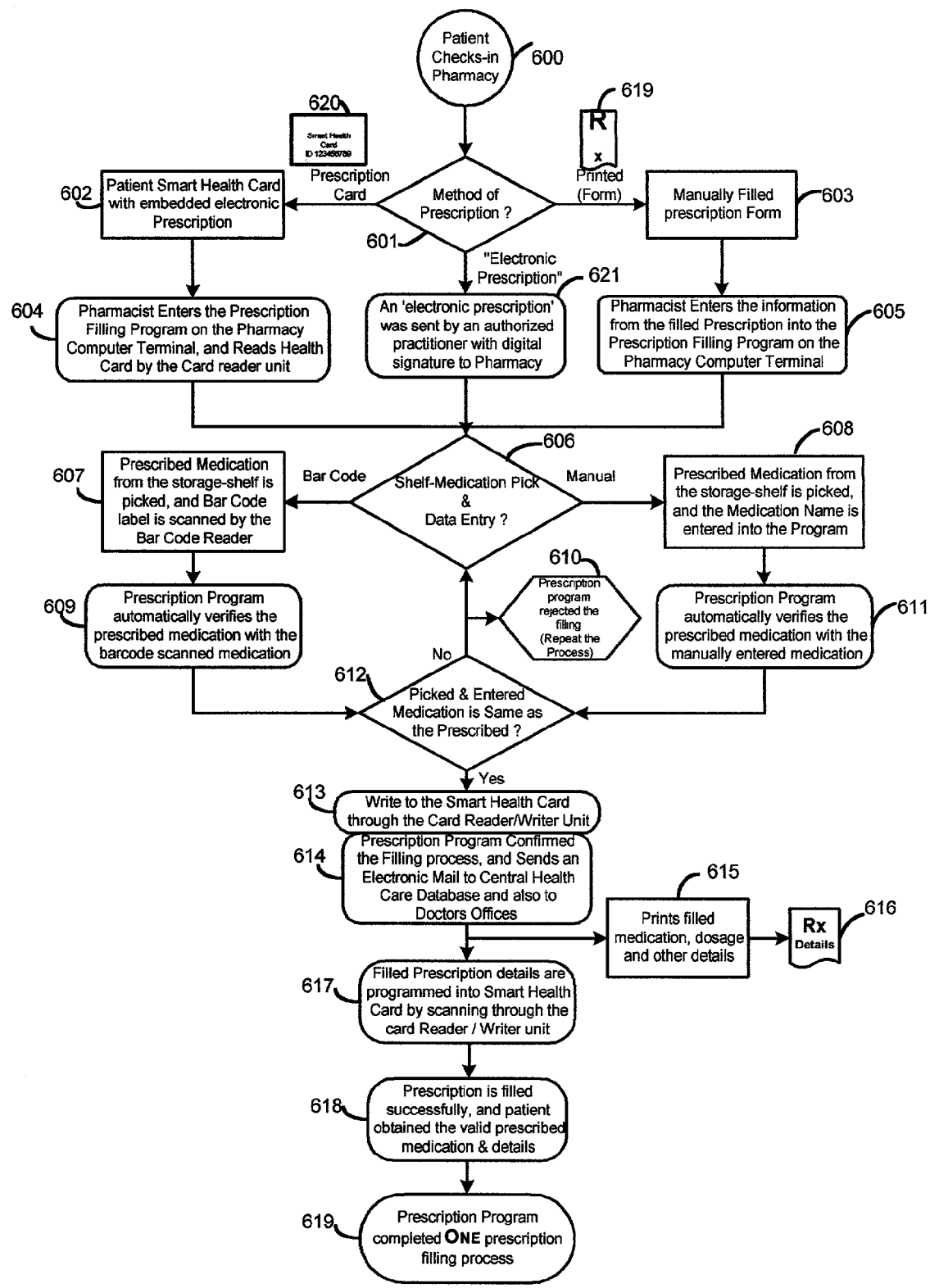
FIG. 6 is a flow chart of the use of the system to fill a prescription in a pharmacy.

FIG. 6 shows the prescription process continued at a pharmacy. The pharmacist places a smart card with a prescription stored in it in the unit in step 602. The pharmacist starts the prescription program, is prompted to authenticate (not shown), and when authenticated reads a prescription from the smart card 604. Alternatively, the pharmacist may choose an option to read the prescription from an "electronic prescription" with a digital signature 621, or to enter the information manually from a written prescription 605. The pharmacist selects the medication from the storage and chooses whether to scan the label or manually enter the medication identity if the label cannot be scanned 606 and either scans the label 607 or manually enters it 608. The program compares the scanned code 609 or entered data 611 to verify that the chosen medication is consistent with the prescription. If not the medication is rejected, if verified the pharmacist is asked to save the fulfillment to the card 613. Electronic confirmation is automatically transmitted to the central database and also to the prescribing practitioner 614. Details are recorded on the smart card and the refills counter decremented 617. In the event that an e-mail electronic prescription was used 621, the electronic confirmations are transmitted when the pharmacist indicates that the prescription is filled 618. Optionally a written record is also printed 615 and 616. The process as shown is operating in the standalone mode. If the process had been carried out in the connected mode the contents of the smart card would have been synchronized with the central database when the card was written to.

Figure 7:
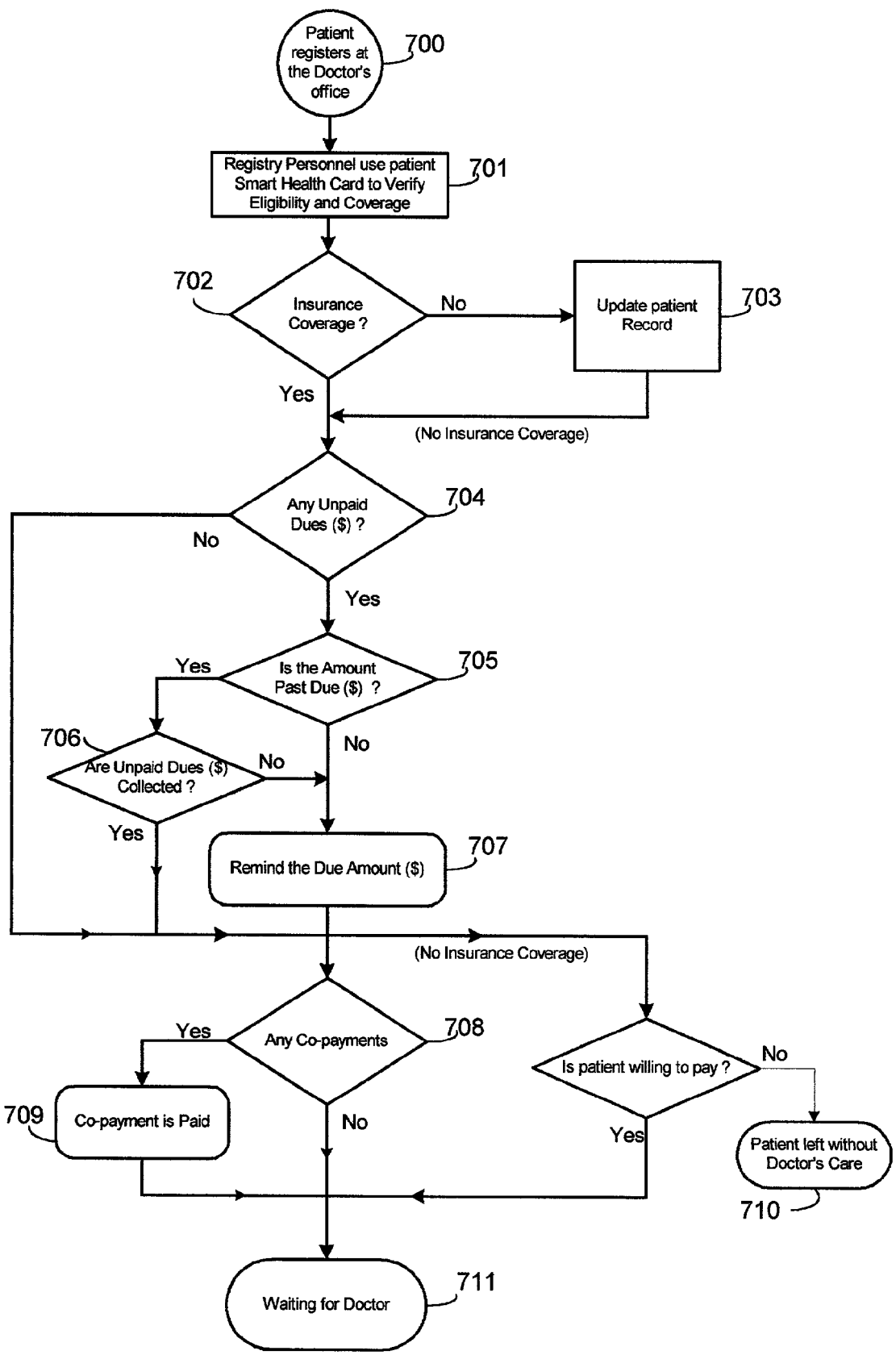
FIG. 7 is a flow chart of the use of the system to check insurance coverage.

FIG. 7 shows an option of the program for checking a patient's insurance status based on information which has been supplied by the insurance provider and downloaded to the smart card when the card is synchronized. The smart card is accessed 701 to verify eligibility and coverage, and the record updated if necessary. The card is checked for a past due balance 704, and if so the amount is collected 706 or service denied 710. The required co-payment is determined 708 and collected 709.

It will be clear that other important health related data can be stored on the smart card and that only certain minimal data has been described. Also as smart card technology develops further there will be a tendency for greater and greater memory to be available on the card which will promote inclusion of more data. One obvious option would to be to include a domain for personal genome data (DNA analysis, gene and phenotype data). In coming years there will be programs available to use this information for diagnosis and treatment.

Another use of the smart card technology coupled with a central data base and local computer systems as described is for marketing and testing pharmaceutical drugs. Maintaining and tracking drug samples which pharmacies have traditionally provided to physicians and clinics to distribute on a trial basis is one example. Tracking these samples (for freshness and content) is burdensome to physicians, and drug manufacturers do not get important feed back on success rate, side effects, and etc. Pharmaceutical companies could issue special smart cards for sample medication, which would be converted into a prescription by a physician and given to the patient to use as an additional health care information system card. The pharmacy would fulfill the prescription and be reimbursed for the cost of trial medications. The physicians' and pharmacy's computer systems would contain additional functionality to notify the pharmaceutical company in addition to each other when a prescription was issued and filled using one of the special smart cards. A patient enrolled in the healthcare information management system benefits in many ways. Patients are enabled to take control of their healthcare records and can make them available selectively to practitioners and other providers, providing a patient with improved capabilities to obtain treatment and services from new practitioners and pharmacies and to immediately provide accurate and current records to a new providers and to preserve the integrity of the patient's comprehensive health records.

Methods and systems are provided whereby a patient can assemble a virtual clinic of otherwise unrelated care providers who have integrated access to the patient's medical records in digital format.

Improved methods are provided for prescribing prescriptions with computer provided assistance, utilizing the comprehensive digital information about the patient and a knowledge base of prescribing information to produce an accurate and safe prescription.

Improved methods are provided for fulfilling prescriptions carried in digital form on a patient's smart card, and utilizing computer provided assistance to verify that the medicine provided to the practitioner is the medicine contained in the prescription, and providing feedback to the prescribing practitioner when the prescription is fulfilled.

Although the present invention has been described in considerable detail with reference to certain preferred versions thereof, other versions are possible. Therefore the spirit and scope of the appended claims should not be limited to the preferred versions herein.

What is claimed is:

1. A method for managing healthcare data which allows a multiplicity of healthcare users to assemble a virtual healthcare clinic, the method comprising the steps of:

a) providing a central data base system capable of holding a multiplicity of health records, pertaining to a multiplicity of patients, wherein said database system is accessible through at least one network connection;

b) enrolling a plurality of healthcare practitioners to create a plurality of enrolled healthcare practitioners, wherein enrolling a healthcare practitioner comprises providing the healthcare practitioner with software operable on a computer system for reading information from medical portable access devices and writing treatment information including medical prescriptions, to said medical portable access devices, to a pharmacy directly by electronic mail and to the central database, and sending and receiving electronic mail, and interacting with the central data base over the at least one network connection;

c) enrolling a plurality of pharmacies to create a plurality of enrolled pharmacies, wherein enrolling a pharmacy comprises providing the pharmacy with software operable on a computer system for reading healthcare information including medical prescriptions written by one of the plurality of enrolled healthcare practitioners from said medical portable access devices, reading medical prescriptions from the central database and reading medical prescriptions from electronic mail, reading a bar-code from a container containing a medicine and determining the identity of the medicine from the bar-code, comparing a medical prescription with the identity of the medicine, and if the identity of the medicine agrees with the medical prescription, writing a confirmation that the medical prescription has been properly dispensed to one of said medical portable access devices, and transmitting a direct electronic message to the one of said plurality of enrolled healthcare practitioners who wrote the medical prescription that the medical prescription was properly filled, and updating the central database that the medical prescription was properly dispensed;

d) enrolling a patient member;

e) providing said patient member with a medical portable access device;

f) programming said medical portable access device provided to said member with healthcare information relevant to said patient member and only said patient member;

g) synchronizing the healthcare information on said medical portable access devices with the healthcare information contained in said central data base; and h) repeating acts (d), (e), (f) and (g) for a multiplicity of patient members creating a multiplicity of enrolled patient members each having a medical portable access device, and wherein any of the multiplicity of enrolled patient members may interact with any combination of enrolled healthcare practitioners and enrolled pharmacies, whereby by each of the multiplicity of enrolled patient members can create a virtual clinic of healthcare providers by choosing enrolled healthcare practitioners and enrolled pharmacies and presenting the portable access device provided to the member for updating at healthcare treatments and prescription fulfillment.

2. The method of claim 1 further comprising the act of providing the multiplicity of patient members with software operable on a computer system for reading the contents of their medical portable access device, and writing updated information on the medical portable access device.

3. The method of claim 1 wherein the multiplicity of medical personal access devices comprise smart cards.

4. The method of claim 1 further comprising providing enrolled healthcare practitioners, and enrolled pharmacies, with software functionality wherein the healthcare information in the central database pertaining to an enrolled patient member is automatically synchronized with the enrolled member's portable access device whenever the enrolled member's portable access device is accessed by either a pharmacy computer system or practitioner computer which is connected to the central data base during access, whereby the central database contains a backup for the portable access devices and has up-to-date information.

5. The method of claim 1, wherein the plurality of enrolled healthcare practitioners comprise representatives from at least three professions chosen from the group consisting of chiropractors, optometrists, dentists, psychologists, opticians, herbalists, podiatrists, and opticians.

6. The method of claim 5 further comprising providing enrolled healthcare practitioners and enrolled pharmacies, with functionality for authenticating the identity of users by a biometric measurement.

7. The method of claim 1, wherein a plurality healthcare practitioners are unrelated except for being enrolled.

8. The method of claim 5, wherein prescriptions contain the digital signature of a healthcare practitioner.

9. A healthcare information system comprising:
a) a central data base system comprising a central data base containing healthcare information pertaining to a multiplicity of patients, said central data base system accessible on at least one external network;
b) a multiplicity of medical portable access devices, wherein each of said multiplicity of patients has at least one medical portable access device;
c) a plurality of healthcare practitioner computer systems, each healthcare practitioner computer system comprising a device for reading and writing to any of said multiplicity of medical portable access devices, an external network communication connection, and software operating said healthcare practitioner computer system, comprising functionality for reading healthcare information pertaining to a patient from said medical portable access devices, writing a record of treatment to said medical portable access devices, writing a prescription to one of said plurality of medical portable access devices, and sending at least one electronic message on the external network when a prescription is written to a portable access device; and
d) a plurality of pharmacy computer systems, each pharmacy computer system comprising a device for reading and writing to any of said plurality of medical portable access devices, an external communication connection, a barcode reader, and software operating said pharmacy computer system, comprising functionality for reading healthcare information pertaining to a patient from said medical portable access devices, reading a prescription for a prescribed medicine from said medical portable access devices, reading a prescription for a prescribed medicine from a direct electronic message, reading a prescription a prescribed medicine from the central database reading a barcode on a package of medicine, determining the identity of the medicine from the barcode, comparing the identity of the medicine with the prescribed medicine, if the identity of the medicine and the prescribed medicine are identical, automatically sending a direct electronic confirmation over the network to an enrolled healthcare practitioner that a prescription has been properly dispensed and decrementing a refills counter pertaining to a filled prescription to said portable access devices.

10. The healthcare information system of claim 9 further comprising a multiplicity of patient computer systems, each patient computer system comprising a device for reading and writing to any of said plurality of medical portable access devices, an external communication connection, and software operating said patient computer system, comprising functionality for reading healthcare information pertaining to a patient from said portable access devices, and writing updated health history information to said portable access devices.

11. The healthcare information system of claim 10 wherein said healthcare provider computer systems, said pharmacy computer systems and said patient computer systems further comprise software functionality for optional connection to said central database system, obtaining information from said central database system, and synchronizing a portable access device to the central database system automatically whenever the portable access device is accessed while a computer system is connected to the central database system.

12. The healthcare information system of claim 11 wherein said healthcare provider computer systems, said pharmacy computer systems, and said patient computer systems further comprise a biometric measurement device for authenticating users.

13. The healthcare information system of claim 12 wherein the healthcare provider computer systems comprise functionality requiring biometric authentication before accessing a medical portable access device.

14. The healthcare information of claim 12 wherein said healthcare provider computer systems, said pharmacy computer systems, and said patient computer systems further comprise software functionality for requiring biometric identification of a user using said biometric measurement device prior to use.

* * * * *